United States Patent [19]

Sioshansi

[11] Patent Number: 4,693,760
[45] Date of Patent: Sep. 15, 1987

[54] ION IMPLANATION OF TITANIUM WORKPIECES WITHOUT SURFACE DISCOLORATION

[75] Inventor: Piran Sioshansi, Bedford, Mass.

[73] Assignee: Spire Corporation, Bedford, Mass.

[21] Appl. No.: 861,845

[22] Filed: May 12, 1986

[51] Int. Cl.$^4$ ............................................. C23C 11/10
[52] U.S. Cl. ....................................... 148/4; 148/421; 148/900; 204/192.31
[58] Field of Search ..................... 148/421, 133, 4, 39, 148/900; 204/192 N

[56] References Cited

U.S. PATENT DOCUMENTS

| | | | |
|---|---|---|---|
| 4,465,524 | 8/1984 | Dearnaley et al. | 148/421 |
| 4,490,190 | 12/1984 | Speri | 148/4 |
| 4,568,396 | 2/1986 | Vardiman | 148/421 |

FOREIGN PATENT DOCUMENTS 2154450  9/1985  United Kingdom .

OTHER PUBLICATIONS

P. Sioshansi et al., "Wear Improvement of Surgical Titanium Alloys by Ion Implantation," J. Vac. Sci. Tech. A3 (6), Dec. 1985, pp. 2670–2674.
P. Sioshansi, "Ion Brass Modification of Materials for Industry", Thin Solid Films, 118 (12/1984), pp. 61–71.
J. M. Williams et al., "Ion Implantation of Surgical Ti-6Al-4V Alloy," Int'l Conference, Hidelberg, F.R.G., Sep. 17–21, 1984.
W. C. Oliver et al., "The Wear Behavior of Nitrogen-Implanted Metals," Met. Trans. 15A, Dec. 1984, pp. 2221–2229.

Primary Examiner—L. Dewayne Rutledge
Assistant Examiner—S. Kastler
Attorney, Agent, or Firm—Morse, Altman & Dacey

[57] ABSTRACT

A process for preventing surface discoloration in orthopedic implants made of titanium and its alloys is disclosed. Such surface discoloration is apt to occur when the orthopedic implants are ion implanted to improve their wear characteristics. The process essentially includes exposing all fixtures and shields, made of pure titanium, located in an implant chamber, to an ion beam, creating a vacuum within the chamber not exceeding about $5 \times 10^{-5}$ torr, introducing an orthopedic implant within the chamber to be directly exposed to the beam, and reducing the ion beam current power density so as not to exceed about 1.0 watt/cm$^2$. Exposing the fixtures and shields to the ion beam first serves to remove surface contamination therefrom, followed by forming a surface layer thereon. This surface layer effectively lowers the sputtering coefficient of the fixtures and shields, and thus reduces the amount of material sputtered from areas exposed to the ion beam to unexposed areas. Preferably, the vacuum is created by using an oil-free vacuum pump.

9 Claims, 7 Drawing Figures

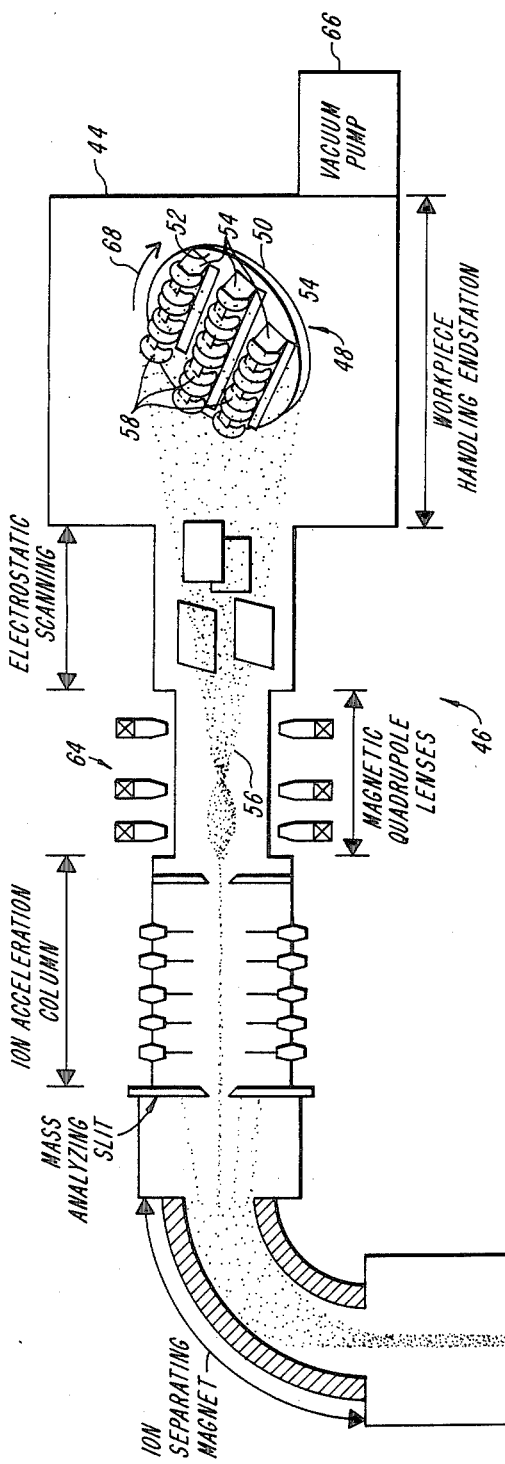
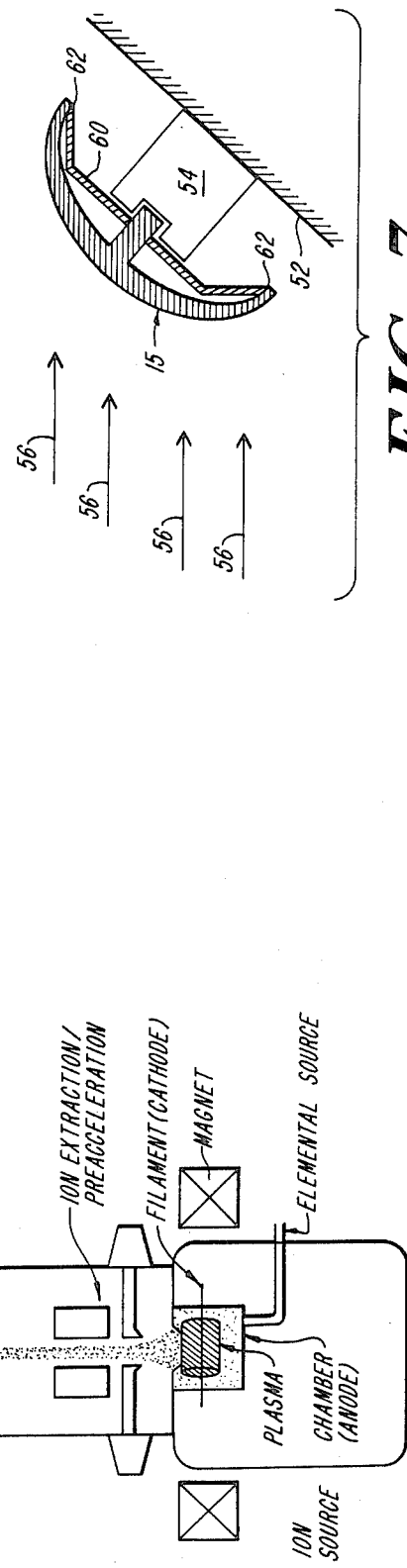
FIG. 6
FIG. 7

ION IMPLANATION OF TITANIUM WORKPIECES WITHOUT SURFACE DISCOLORATION

BACKGROUND OF THE INVENTION

1. Field of the Invention

The present invention relates generally to processing titanium alloy workpieces and, more particularly, to a process of preventing surface discoloration of workpieces formed of titanium and its alloys during their ion implantation.

2. The Prior Art

Titanium-based alloys have come to the fore of late in replacing cobalt-based alloys that had been traditionally used as orthopaedic surgical implants. A number of reasons are responsible for the switch to titanium-based alloys. These include: excellent tensile strength, high fatigue strength, low density, high corrosion resistance, substantial ductility, a low modulus of elasticity compatible with bone structure that facilitates good adhesion thereto and, most importantly, excellent biocompatibility. The only questionable property of titanium-based alloys has proven to be their wear resistance. The poor wear performance of surgical implants made from titanium-based alloys has however been effectively improved upon by ion implantation, in particular by implantation of carbon and nitrogen ions directly into the surface of the surgical implants. See "Ion Beam Modification of Materials for Industry", *Thin Solid Films*, 118 (1984) 61–71; "The Wear Behavior of Nitrogen-Implanted Metals," *Metallurgical Transactions*, A 15 (1984), 2221–2229; and "Wear improvement of surgical titanium alloys by ion implantation"; *J. Vac. Sci. Tech.* A3 (6) Nov./Dec. 1985, 2670–2674.

While effectively improving the wear performance of titanium-alloy surgical implants, ion implantation of these implants causes the surfaces of the implants to discolor at spots. Such discoloration resembles tarnishing and exhibits a goldish-yellow or bluish color. When viewed by others, in particular by surgeons who perform the operations and by patients slated to receive such orthopedic implants, the sights of these discolored implants make their acceptance less than desirable, if not outright objectionable.

SUMMARY OF THE INVENTION

It is a principal object of the present invention to overcome the above disadvantages by providing a process for preventing the surface discoloration of orthopaedic surgical implants made of titanium and its alloys and occurring during their ion implantation.

More specifically, it is an object of the present invention to provide a process for the prevention of surface discoloration in workpieces, such as used for orthopaedic surgical implants and made from titanium and its alloys, during their ion implantation designed to improve their wear resistance, the process comprising exposing all of the fixtures and shields made from pure titanium and mounted within an ion implanter chamber to an ion beam so as to condition these fixtures and shields by removing any surface contamination therefrom and by forming a surface layer thereon characterized by possessing a sputtering coefficient lower than that of pure titanium, creating a vacuum in the ion implantation chamber which does not exceed $5 \times 10^{-5}$ and preferably is about $1 \times 10^{-6}$ torr and preferably employing an oil-free vacuum pump to avoid surface discoloration, introducing a workpiece formed of titanium and its alloys into the ion implantation chamber and being secured therein by the conditioned pure titanium fixtures in such a way as to be arranged in a direct line of the ion beam, the beam having an ion beam power density on the surface of the workpiece not exceeding about 1.0 watt/cm$^2$ and preferably being about 0.5 watt/cm$^2$, and exposing the workpiece to the ion beam to ion implant the surface thereof. Preferably, the ion beam incorporates one of a group of elemental species including nitrogen, carbon, chromium, zirconium, oxygen, boron, tin, iron, tantalum, molybdenum, neon, argon krypton and xenon. As a consequence of the process, the surfaces of the workpieces formed of titanium and its alloys will remain of the same natural color and hue after their ion implantation designed to improve their wear performance as they were prior to their ion implantation, i.e., without acquiring any spots of goldish-yellow or bluish discoloration. Consequently, the surgeon now can properly show and display the orthopaedic surgical implant to a prospective patient recipient prior to surgery without fear that the recommended surgery might be cancelled by the patient when shown a spotty-looking implant.

Other objects of the present invention will in part be obvious and will in part appear hereinafter.

The invention accordingly comprises the process of the present disclosure, its steps, components, parts and their interrelationships, the scope of the which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 6 is a schematic view of an ion beam implanter useful in carrying out the process of the invention; and FIG. 7 is a side elevation, partly in section and on an enlarged scale, of a workpiece exposed to the process of the invention according to FIG. 6.

DETAILED DESCRIPTION OF THE PREFERRED EMBODIMENT

Figure 1:
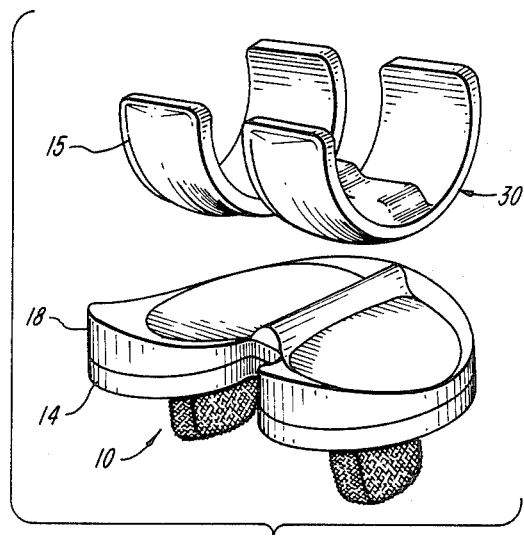
FIG. 1 is a perspective view of an artificial knee joint prosthesis made partly of titanium and its alloys and treated according to the process of the invention and thus presenting a natural-looking surface.

In general, the present invention pertains to a process for preventing surface discoloration from occuring in the surfaces of orthopaedic surgical implants made of titanium and its alloys during their ion implantation designed to improve their wear characteristics.

Recently, titanium-based alloys have come to be preferred for use as orthopaedic surgical implants in lieu of cobalt-based alloys. Advantageous features of titanium-based alloys which make them preferable include excellent tensile strength, high fatigue strength, low density, high corrosion resistance, substantial ductility, a low modulus of elasticity compatible with bone structure that facilitates good adhesion between the bone structure and the alloy and, most importantly, excellent biocompatibility. Titanium and its alloys are strong, light metals that are easily malleable when heated and are ductile, particularly pure titanium. For surgical implantations, the titanium-based alloy, Ti-6Al-4V, has become the most widely used and accepted. Only one undersirable feature of titanium-based alloys has manifested itself over the years, and that has proven to be their poor wear performance. This poor wear performance of surgical implants made from titanium-based alloys recently has been effectively improved upon by ion implantation, in particular by the implantation of carbon or nitrogen ions directly into the surfaces of such orthopaedic surgical implants, see the articles mentioned above. Although effectively improving the wear performance of such surgical implants, the ion implantation of their surfaces has created a new problem caused by the discoloration in the surfaces of the surgical implants. For, such surface discoloration adversely impacts on the acceptability of the surgical implant by both the surgeon and the patient, in whose body the surgical implant is slated to be incorporated.

The appearance of the implant is important. In the first place, each one of a plurality of implants of the same kind, i.e., artificial knees, hips or other articulating joints, including shoulders, elbows or the like, must look exactly the same as all the rest. Different appearances cast doubt on their quality. With quality and its control in doubt, the surgeon will likely use a product from a different manufacturer. Second, some surgeons prefer to illustrate and explain the surgical procedure to the patient by showing him or her an orthopaedic prosthesis just like the one designed to replace the damaged hip or knee joint. A discolored prosthesis simply cannot be so used, however. Ordinarily, titanium and titanium-based alloys, including the preferred surgical Ti-6Al-4V alloy, have a lustrous, silvery-gray appearance. When their surfaces are implanted by nitrogen and carbon ions however so as to improve their wear performance, goldish-yellow and/or bluish spots, resembling tarnishing, show up on the surfaces. These spots are of varied size and shape and, for the most part, exhibit jagged edges. When appearing on the natural lustrous, silvery-gray surface of the implant, the spots make for an arresting view, sufficient to discourage most patients from wanting such a prosthesis permanently placed in their body. The process of the invention has been developed to prevent such discolorations from occurring during the ion implantation of the orthopaedic implants, which ion implantation is required to improve their wear performance. When titanium and its alloys are treated according to the process of the invention, the workpieces made therefrom retain their natural surface appearance, i.e., a lustrous, silver-gray color, free of any spots of discoloration.

Figure 3:
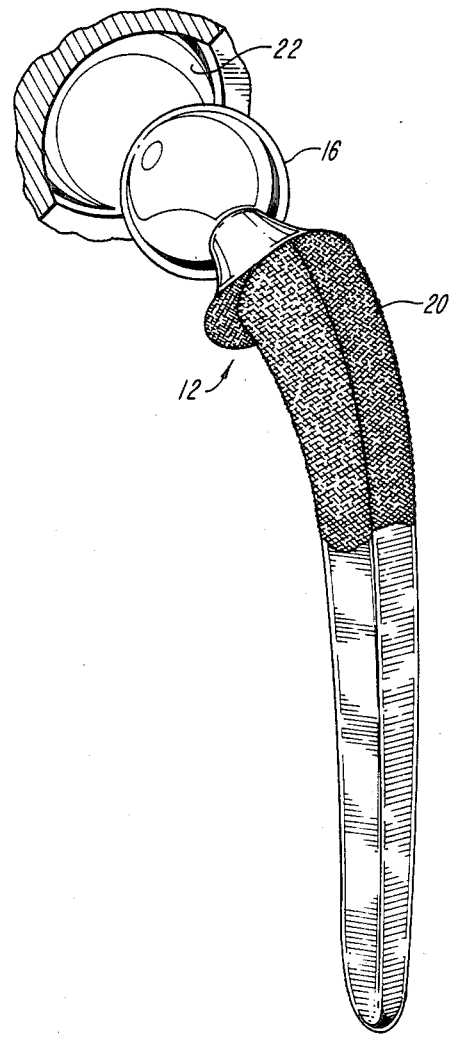
FIG. 3 is a perspective view of an artificial hip-joint prosthesis made partly of titanium and its alloys and treated according to the process of the invention and thus presenting a natural-looking surface.

In FIGS. 1 and 3 are illustrated artificial prostheses for a knee joint 10 in the former and for a hip joint 12 in the latter. Each prosthesis 10 and 12 comprises at least one element formed of metal and a complementary mating element formed of plastic. The knee joint prosthesis 10 thus is formed of two metal parts 14 and 15, separated by a plastic part 18. The parts 14 and 15 preferably are formed of a titanium alloy, such as the surgical Ti-6Al-4V alloy. The plastic part 18 on the other hand is preferably formed of ultrahigh molecular weight polyethylene (UHMWPE). In like fashion, the hip joint prosthesis 12 is formed of a metal part 20 having a hemispherical ball portion 16, preferably formed of surgical Ti-6Al-4V alloy, and a plastic part 22, also preferably formed of UHMWPE. It is understood that the metal part 20 is placed into the femur, either by a cemented or cementless process. The low elastic modulus feature of the surgical Ti-6Al-4V alloy contributes significantly to improved load sharing in the alloy-bone or alloy-cement-bone composite of the upper femur. During walking, the alloy ball portion 16 works against the UHMWPE cup part 22. In like fashion, the metal part 15 of the knee joint prosthesis 10 works against the UHMWPE part 18 during walking. The conditions of loading, sliding velocity and body chemistry that obtain in the respective knee and hip prostheses 10 and 12 are such as tending to produce corrosion, wear and a combination thereof in the titanium alloy and/or the UHMWPE component.

As mentioned, titanium based alloys excell in all properties over cobalt-based alloys, excepting wear performance. Such poor wear performance has been effectively improved upon by ion implantation of carbon and nitrogen ions directly into the surface of the finished titanium alloy components 15 and 20 of the knee and hip joint prostheses 10 and 12, respectively. The ion implantation also improves the corrosion resistance properties of the titanium alloy. This has been substantiated by subjecting the titanium alloys to various chemical analyses, including employing polarization corrosion studies.

Figure 2:
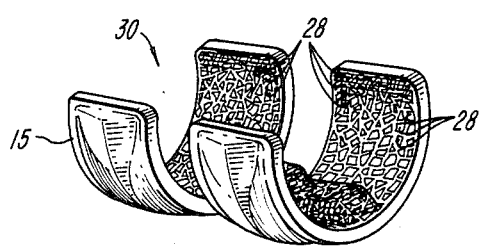
FIG. 2 is a view of a titanium alloy part of an artificial knee joint posthesis, like the one shown in FIG. 1, but not treated according to the process of the invention and thus presenting unwanted surface discolorations thereon.
Figure 4:
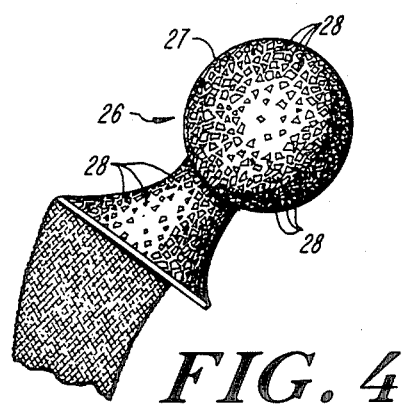
FIG. 4 is a fragmentary view of a titanium alloy component of an artificial hip-joint prosthesis like the one shown in FIG. 3, but not treated according to the process of the invention and thus presenting unwanted surface discolorations on its surface.

Also as mentioned, the ion implantation of the metallic parts 15 and 20 causes surface discoloration of the parts, which make them aesthetically less than desirable both to orthopaedic surgeons and their patients slated for prosthetic implants. FIGS. 2 and 4 illustrate the problem that the process of the invention is designed to prevent. FIG. 2 is a view of a part 24 formed of a titanium alloy, such as surgical Ti-6Al-4V alloy, which part 24 has been ion implanted with nitrogen ion, producing a concentration of about 20 at. % N to a depth of about 100 nm below the part's 24 surface, as required for improving its wear performance. FIG. 4 is a fragmentary view of a ball part 26 formed of a titanium alloy, such as surgical Ti-6Al-4V alloy, which part 26 also has been ion implanted with nitrogen ion so as to produce a concentration of about 20 at. % N to a depth of about 100 nm below its surface, as required for improving its wear performance. The surfaces 25 and 27 of both parts 15 and 26 exhibit unwanted discolorations 28. For the most part, these discolorations 28 are goldish-yellow or bluish-yellow and, like tarnishing of the metal, appear at certain locations. Appearing, as these discolorations 28 do, on the natural looking surfaces 25 and 27 which are a lustrous, silvery-gray, they do have a tendency to adversely affect patients, when exposed to it. Since orthopaedic surgical implants, such as the illustrated knee and hip joint prostheses 10 and 12 herein, are expected to last about ten years, it is hardly surprising when a patient looks askance at such a discolored prosthesis. The discolorations 28 of the surfaces 25 and 27 are titanium nitride or titanium oxynitride, TiON, which are sputter deposited onto the surfaces 25 and 27 from parts located within the workpiece handling end station due to sputtering by the ion beam.

Figure 5:
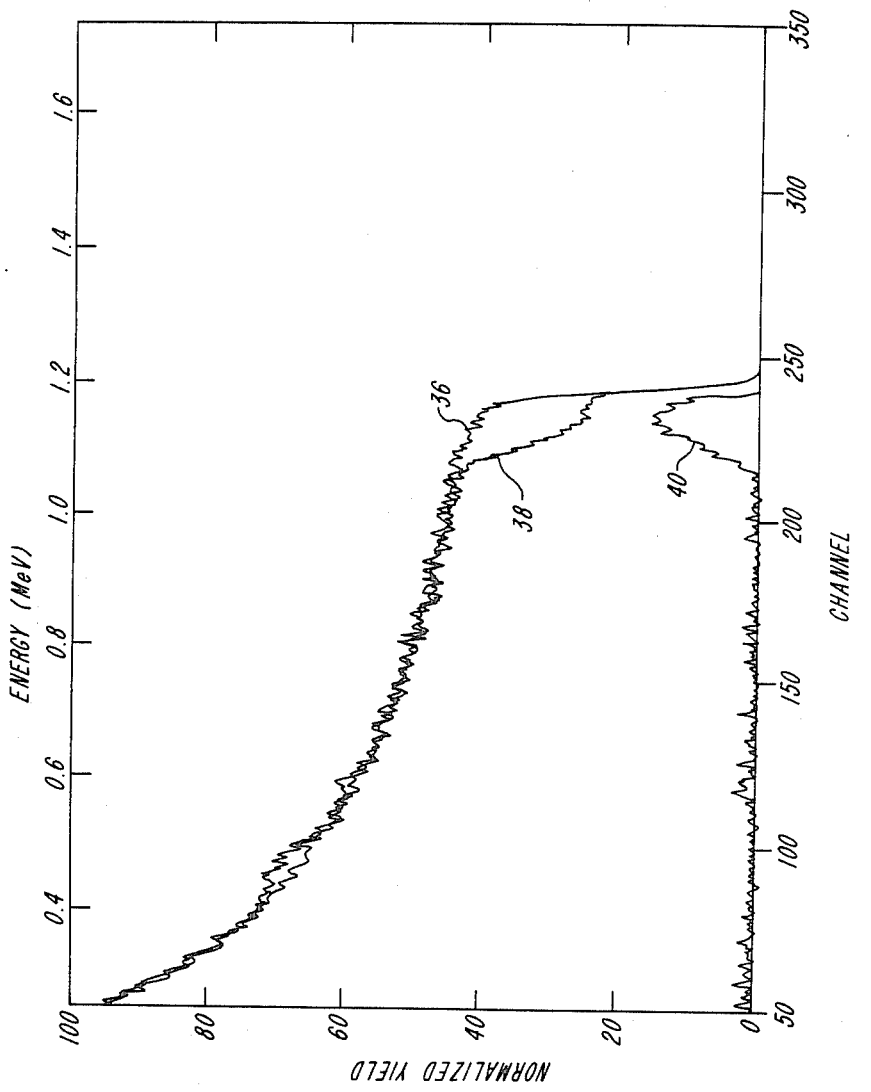
FIG. 5 depicts measurement curves helpful in understanding the process of the invention.

In FIG. 5 are depicted RBS measurement curves of an unimplanted sample 36 versus an implanted sample 38 formed of titanium. The sample 38 implanted with nitrogen ion has been implanted with a dose of at least about $2 \times 10^{17}$ nitrogen ions/cm² and, preferably with a dose of about $3 \times 10^{17}$ nitrogen ions/cm². The measured data show that the implanted sample 38 has a high concentration of nitrogen and oxygen on its surface (TiON), as indicated by the curve 40. These TiON compounds on the surfaces of the workpieces 24 and 26 are mainly responsible for the discolorations 28 thereon.

The process of the invention for preventing these surface discolorations 28 of workpieces 24 and 26 formed of titanium and its alloys during their ion implantation is preferably carried out in a suitable implant chamber 44 of a specially designed endstation 46 of a suitable high current ion implanter, such as a Varian-Extrion 200 kV implanter, an Eaton-Nova implanter or a like instrument. The endstation 46 is illustrated in FIG. 6.

Within the implantation chamber 44, a suitable fixture 48 is mounted on a base 50 designed for rotating and cooling a titanium base plate 52. On the base plate 52 are mounted a plurality of appropriately shaped workpiece holders 54, also made of titanium. These workpiece holders 54 are designed to hold securely a plurality of workpieces 58 and directly expose these workpieces 58 to an incoming ion beam 56. The illustrated workpieces 58 are the titanium alloy parts 15 of the knee joint prosthesis illustrated in FIG. 1. It is to be understood that the shape of the particular workpiece holders secured to the base plate 52 will depend upon the shape of the particular workpieces worked on at that time. In FIG. 7 is illustrated one such workpiece, a titanium alloy part 15 secured to one of the workpiece holders 54.

As evident from viewing FIG. 7, the fixture 48 is so designed as to expose, at one time or another, all surfaces of the workpieces directly to the ion beam 56. Any surface of the workpiece which cannot be exposed directly to the ion beam 56 must be shielded by a titanium shield 60. It is imperative that the shield 60 fit flush with the edges of the part 15 in the back, as at 62. This flush-fitting is important to prevent the ion beam 56 from sputtering around the corners of the part 15 and thus discolor the part 15 in the back.

In the practice of the process of the invention, it is important that first all titanium fixtures 48 and shields 60 be conditioned or seasoned by being exposed to a full ion implantation dose before performing any ion implantation on titanium alloy parts within the implantation chamber 44. Such a full ion implantation dose preferably is about $3 \times 10^{17}$ ions/cm² at the surfaces of the titanium fixtures and shields, and extending about 100 nm below those surfaces. Such a dose preferably is effected with the ion beam 56 applied to the surfaces for a period of about three and a half hours, with an ion beam particle energy from about 10 keV to about 200 keV. The ion beam 56 preferably incorporates one of a group of elemental species, including nitrogen, carbon, chromium, zirconium, oxygen, boron, tin, iron, tantalum, molybdenum, neon, argon krypton and zenon.

The conditioning or seasoning of the surfaces of all titanium fixtures and shields within the implantation chamber 44 achieves two important functions: first it serves to remove any surface contamination and titanium compounds that may be present on the surfaces of these titanium fixtures and shields and, second it serves to form an appropriate surface layer, such as titanium nitride (TiN), if nitrogen was the elemental species of the ion beam 56. The composition of this surface layer will, of course, depend which one of the elemental species, mentioned above, is incorporated in the ion beam 56. This newly formed surface layer, such as the titanium nitride (TiN) layer, possesses a considerably lower sputtering coefficient, i.e., between about 0.06 and 0.09 at 50 keV for N+ than does pure titanium, whose sputtering coefficient is about 0.3 for 50 keV N+. It will be recalled that the titanium fixtures 48 and shields 60 within the implantation chamber 44 are formed of pure titanium. As stated, it is the sputtering of titanium compounds during the ion implantation of the parts 15 and 20 which is one of the causes of the discolorations 28. The seasoning of these pure titanium fixtures 48 and shields 60 thus effectively removes this source of potential discoloration, i.e., any sputtering of titanium compounds from those fixtures 48 and shields 60 onto the parts 15 and 20, during their ion implantation.

The next step of the process of the invention involves the creation of a proper vacuum environment within the implantation chamber 44. For, it is an improper vacuum environment within the implantation chamber 44 during the ion implantation of the parts 15 and 20 which is another cause of the discoloration 28. To this end, a vacuum within the implant chamber 44 must be created which is less than about $5 \times 10^{-5}$ and preferably is about $1 \times 10^{-6}$ torr, averaged during the ion implantation period of the parts 15 and 20. With the proper vacuum established within the implant chamber 44, with the air of a suitable vacuum pump 66, a plurality of the workpieces 58 are introduced within the chamber 44. Preferably, the vacuum pump 66 should be of an oil-free type so as to avoid the possibility of introducing surface contamination onto the part to be ion implanted. The actual sequence of the two steps preferably is reversed, i.e., the workpieces 58 first are introduced into the chamber 44 and mounted therein in the fixtures 48, followed by the pump-down of the proper vacuum therein, it being of important only that during the ion implantation step itself the proper average vacuum prevails, as above specified.

With the titanium and its alloy workpieces 58 secured in the pure titanium fixtures 48 within the chamber 44, the workpieces 58, in particular their respective surfaces, are exposed to a direct line of the incoming ion beam 56. In order to achieve such a direct line, the fixture 48 is caused to rotate on its base 50 by motors not shown, as indicated by an arrow 68. The sputtering of titanium compounds occurs at the surfaces of the workpieces 58 from their exposed to their unexposed areas. Careful attention must also be paid to having the proper ion beam power density acting on the surfaces of the workpieces 58. For, if the ion beam power density is too high in certain areas, localized heating may well occur, which in turn will further contribute to causing the discolorations 28. This ion beam power density acting on the surfaces of the workpieces cannot exceed about 1.0 watt/cm² and preferably is about 0.5 watt/cm². Consequently, the peak ion beam power density of an 50 keV beam should not exceed about ten microamperes per square centimeter.

The control of the ion beam power density can be achieved in a number of ways. Preferably, and as herein illustrated, this low power ion beam current density is effected by expanding the spot size of the incoming ion beam 56 (observe FIG. 6) by a magnetic quadrupole or an electro-static lens system 64. The surfaces of the workpieces 58, now secured in the fixture 48 within the implant chamber 44, are then exposed to the incoming ion beam 56, properly modified, if need be, by the lens system 64, for a period from about three hours to about four hours, and preferably for a period of about three and a half hours, with a preferred ion beam particle energy of about 50 keV, so as to implant a dose of at least about $3 \times 10^{17}$ ions/cm$^2$ and to a depth of about 100 nm below the surfaces of the workpiece 58. The result is that the ion implanted surfaces of the workpieces 58 will retain their natural sheen, i.e., the lustrous, silvery-gray surface finish of titanium and its alloys, free of any discolorations 28, as if they had not been ion implanted at all. In any areas where slight discolorations 28 are nevertheless noted, these also can be removed by a further exposure to the ion beam 56.

Thus it has been shown and described a process for preventing surface discolorations from occurring in orthopaedic implants made from titanium and its alloys during their ion implantation designed to improve their wear performance, which process satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A process for preventing surface discoloration of workpieces formed of titanium and its alloys during their ion implantation wherein a plurality of workpieces are exposed to an ion beam in series so as to improve their wear performance comprising:
   (a) exposing all titanium fixtures and shields mounted within an implant chamber prior to each ion implantation to an ion beam so as to cleanse them of surface contamination and to form a surface layer thereon having a sputtering coefficient lower than that of titanium;
   (b) creating a vacuum within said implant chamber not exceeding about $5 \times 10^{-5}$ torr; and
   (c) introducing a workpiece formed of titanium and its alloys into said implant chamber to be secured therein by said cleansed and surface layer coated titanium fixtures and exposing said workpiece to a direct line of said ion beam while shielding areas thereof not being treated;
   (d) said ion beam having an ion beam power density on the surface of said workpiece not exceeding about 1.0 watt/cm$^2$;
   (e) said ion beam incorporating one of a group of elemental species consisting of nitrogen, carbon, chromium, zirconium, oxygen, boron, tin, iron, tantalum, molbdenum, neon, argon, krypton and xenon.

2. The process of claim 1 wherein said exposing said titanium fixtures and shields to said ion beam is for a period of about three and a half hours, with an ion beam particle energy from about 10 keV to about 200 keV so as to implant a dose of about $3 \times 10^{17}$ ions/cm$^2$, and wherein the peak current density of said ion beam does not exceed about ten microamperes/cm$^2$.

3. The process of claim 1 wherein said ion beam power current density is achieved by expanding the spot size of said ion beam by a magnetic lens system surrounding said incoming ion beam.

4. The process of claim 1 wherein said ion beam power current density is achieved by expanding the spot size of said ion beam by an electrostatic lens system acting on said incoming ion beam.

5. The process of claim 1 wherein said workpiece includes orthopaedic surgical implants for use as artificial knee and hip joints.

6. A process for preventing surface discoloration of workpieces formed of titanium and its alloys during their ion implantation wherein a plurality of workpieces are exposed to an ion beam in series so as to improve their wear performance comprising:
   (a) exposing all fixtures and shields mounted within an implant chamber and formed of pure titanium to an ion beam prior to each implantation so as to cleanse them of surface contamination;
   (b) creating a vacuum within said chamber not exceeding about $5 \times 10^{-5}$ torr;
   (c) introducing a workpiece formed of titanium alloy into said chamber;
   (d) said ion beam having an ion beam power current density on the surface of said workpiece not exceeding about 1.0 watt/cm$^2$; and
   (e) exposing said workpiece to a direct line of said ion beam to ion implant the same;
   (f) said exposing said pure titanium fixtures and shields to said ion beam first sputter-cleans the surfaces thereof, followed by forming a surface layer thereon possessing a sputtering coefficient lower than that of pure titanium;
   (g) said titanium alloy being Ti-6Al-4V and said vacuum being created by using an oil-free vacuum pump;
   (h) said ion beam incorporating one of a group of elemental species consisting of nitrogen, carbon, chromium, zirconium, oxygen, boron, tin, iron, tantalum, molybdenum, neon, argon, krypton and xenon.

7. The process of claim 6 wherein said exposing said titanium fixtures and shields to said ion beam is for a period of about three and a half hours, with an ion beam particle energy from about 10 keV to about 200 keV so as to implant a dose of about $3 \times 10^{17}$ ions/cm$^2$.

8. The process of claim 6 wherein said exposing said workpiece to said ion beam extends for a period of about three and a half hours, with an ion beam particle energy from about 10 keV to about 200 keV so as to implant a dose of at least about $3 \times 10^{17}$ ions/cm$^2$.

9. The process of claim 6 wherein said sputtering coefficient of said surface layer is about 0.06, and does not exceed 0.09.

* * * * *